US011913961B2

(12) United States Patent
Fogelstrand et al.

(10) Patent No.: US 11,913,961 B2
(45) Date of Patent: *Feb. 27, 2024

(54) METHOD FOR PREPARING A BIOLOGICAL SAMPLE FOR USE IN AN IMMUNOLABELING PROCESS

(71) Applicant: Kromnigon AB, Gothenburg (SE)

(72) Inventors: Per Fogelstrand, Mölndal (SE); Ulf Yrlid, Gothenburg (SE)

(73) Assignee: B KROMNIGON, Gothenburg (SE)

( * ) Notice: Subject to any disclaimer, the term of this patent is extended or adjusted under 35 U.S.C. 154(b) by 215 days.

This patent is subject to a terminal disclaimer.

(21) Appl. No.: 15/543,465

(22) PCT Filed: Jan. 18, 2016

(86) PCT No.: PCT/SE2016/050027
§ 371 (c)(1),
(2) Date: Jul. 13, 2017

(87) PCT Pub. No.: WO2016/118065
PCT Pub. Date: Jul. 28, 2016

(65) Prior Publication Data
US 2018/0003718 A1    Jan. 4, 2018

(30) Foreign Application Priority Data

Jan. 19, 2015 (SE) .................... 1550041-6

(51) Int. Cl.
*G01N 33/53* (2006.01)
*G01N 33/68* (2006.01)
*G01N 33/542* (2006.01)
*G01N 33/58* (2006.01)

(52) U.S. Cl.
CPC ..... *G01N 33/6854* (2013.01); *G01N 33/5306* (2013.01); *G01N 33/542* (2013.01); *G01N 33/58* (2013.01); *G01N 2474/20* (2021.08)

(58) Field of Classification Search
CPC ........... G01N 33/6854; G01N 33/5306; G01N 33/542; G01N 33/58; G01N 33/53; G01N 2470/00; G01N 2470/04; G01N 2470/06; G01N 2470/10; G01N 2470/12; G01N 2474/20
USPC ....................................... 436/540
See application file for complete search history.

(56) References Cited

U.S. PATENT DOCUMENTS

| 2006/0286546 A1 | 12/2006 | Ramael et al. | |
| 2007/0099248 A1 | 5/2007 | Ting et al. | |
| 2008/0167243 A1* | 7/2008 | Schultz | C12P 19/26 |
| | | | 435/70.1 |
| 2008/0286881 A1 | 11/2008 | Apel et al. | |
| 2010/0285490 A1* | 11/2010 | Dees | G01N 33/54373 |
| | | | 435/7.1 |
| 2012/0171763 A1 | 7/2012 | Katayose | |
| 2012/0214187 A1* | 8/2012 | Lees | G01N 33/548 |
| | | | 435/7.95 |
| 2014/0315761 A1 | 10/2014 | Beaman | |
| 2016/0258956 A1* | 9/2016 | Schwartz | G01N 33/54306 |
| 2017/0045502 A1* | 2/2017 | Ohbayashi | G01N 33/536 |

FOREIGN PATENT DOCUMENTS

| EP | 0389301 A2 | 9/1990 | |
| EP | 0389301 A3 | 9/1990 | |
| EP | 2669296 A1 | 12/2013 | |
| EP | 1488000 * | 3/2014 | ........... G01N 33/353 |
| GB | 2098730 A | 11/1982 | |
| SE | 1550041 A1 | 7/2016 | |
| WO | 9727486 A1 | 7/1997 | |
| WO | WO 2007/096637 * | 8/2007 | ........... G01N 33/558 |
| WO | 2009032128 A1 | 3/2009 | |
| WO | 2013038272 A2 | 3/2013 | |
| WO | 2014163557 A1 | 10/2014 | |
| WO | 2016118065 A1 | 7/2016 | |

OTHER PUBLICATIONS

Wierdorn et al. (The Journal of Histochemistry and Cytochemistry).*
Howarth et al. (Nature Methods vol. 3 No. 4, 2006, p. 267-273).*
Vincent et al. (Journal of Immunological Methods, 1993; vol. 165, issue 2, pp. 177-182, abstract).*
Anti-c-myc Antibody (2010, retrieve from http://www.aveslab.com/products/epitope-tag-and-gfp-antibodies/ fluorescein-fitc-labeled-anti-c-myc-antibodies/.*
Secondary Antibody Selection (2002;retrieved from https://www.ptglab.com/news/blog/secondary-antibody-selection/) .*
E. A. Padlan, Adv Prot Chem 49:57-133; 1996 (PTO-892).*
Corada et al., Blood, 2001; 97:1679-84.*
Kuby et al. Immunology, W.H. Freeman and Company (1992), p. 125.*
Wolfe, S.L., Molecular and Cellular Biology, 1993, pp. 790-793), Academic Press Dictionary of Science and Technology.*
Park et al. Journal of Immunological Methods vol. 331, Issues 1-2, Feb. 29, 2008, pp. 27-38.*
European Search Report for EP Application No. 16740471.4 dated May 7, 2018, 6 pages.
Carayanniotis, G., et al., "Adjuvant-independent immunization by immunotargeting antigens to MHC and non-MHC determinants in vivo", Molecular Immunology, 1991, vol. 28, No. 3, pp. 261-267.
Hosokawa, K., et al., "Immunoassay on a power-free microchip with laminar flow-assisted dendritic amplification", Analytical Chemistry, 2007, vol. 79, No. 15, pp. 6000-6004.

(Continued)

*Primary Examiner* — Carmencita M Belei
(74) *Attorney, Agent, or Firm* — RMCK Law Group, PLC

(57) ABSTRACT

The present invention generally relates to method for preparing a biological sample for use in an immunolabeling process. The invention also relates to corresponding kits for use in the immunolabeling process.

9 Claims, 3 Drawing Sheets

(56) References Cited

OTHER PUBLICATIONS

International Search Report and Written Opinion for International Application No. PCT/SE2016/050027 dated Apr. 6, 2016, 12 pages.
Chinese Office Action for Chinese Application No. 201680000651 2.6 dated May 22, 2018 with English translation, 15 pages.
European Search Report for EP Application No. 16740472.2 dated May 4, 2018, 7 pages.
Haugland, Rosaria P., "Antibody Conjugates for Cell Biology" in: "Current Protocols in Cell Biology" Supplement 6, (2000), pp. 16.5.1-16.5.22.
Im, Kok Hong, et al., "Stable, high-affinity streptavidin monomer for protein labeling and monovalent biotin detection", Biotechnology and Bioengineering, vol. 110, No. 1, Jan. 2013, pp. 57-67.
Taylor, Steven K., et al., "Monovalent Streptavidin that Senses Oligonucleotides", Angewandte Chemie International Edition, vol. 52, No. 21, May 17, 2013, 9 pages.
communication Pursuant to Article 94(3) EPC dated Dec. 9, 2019 from European Patent Office for EP Application No. 16740471A, 4 pages.

* cited by examiner and Swedish Application No. 1550041-6, filed on Jan. 19, 2015. The disclosures of each of the above applications are incorporated herein by reference in their entirety.

METHOD FOR PREPARING A BIOLOGICAL SAMPLE FOR USE IN AN IMMUNOLABELING PROCESS

CROSS-REFERENCE TO RELATED APPLICATIONS

This application is a 371 U.S. National Stage of International Application No. PCT/SE2016/050027, filed Jan. 18, 2016, which claims priority to Swedish Application No. 1550041-6, filed on Jan. 19, 2015. The disclosures of each of the above applications are incorporated herein by reference in their entirety.

TECHNICAL FIELD

The present invention generally relates to method for preparing a biological sample for use in an immunolabeling process. The invention also relates to corresponding kits for use in the immunolabeling process.

BACKGROUND OF THE INVENTION

In immunolabeling, antibodies are used for detection of molecules in biological and non-biological samples. Antibodies are immunoglobulin (Ig) proteins that bind with high specificity through its antigen-binding site to an antigen (target molecule). Typically the antigen is a protein, but can be any immunogenic agent such as a shorter amino acid sequence (peptide), polysaccharide, lipid, toxin etc. The part of the target molecule to which the antibody binds is called epitope. Antibodies used for immunolabeling can be polyclonal or monoclonal. Polyclonal antibodies are a heterogeneous mix of antibodies that recognize several epitopes of one target molecule, while monoclonal antibodies show specificity for a single epitope. In general, monoclonal antibodies render more specific immunolabeling signals than polyclonal antibodies.

The final step in immunolabeling is detection of a signal from the antibodies that has bound to the antigens in the sample. The signal is generated from some kind of reporter molecule. The reporter molecule can either be directly attached to the primary antibody, or attached to a secondary antibody that recognizes the primary antibody. Often several reporter molecules are attached to each antibody molecule. The reporter molecules used in immunolabeling vary depending on the nature of the detection method. The most common reporter molecules are enzymes for chromogenic detection or fluorochromes for fluorescence signals. Other examples are particles (e.g. gold particles, quantum dots), phosphorescent compounds (e.g. carboxyamide dyes), radioactive compounds (e.g. 3H or 32P labeled molecules) and transition metals (for mass spectrometry).

Immunolabeling can either be direct or indirect. The direct method is a one-step immunolabeling method and involves a primary antibody that is labeled with a reporter molecule. When the labeled primary antibody is added to a sample it binds to its corresponding target antigen in the sample and reveals the location and/or amount of the target molecule. Since the direct method utilizes only one step it is simple and rapid. However, in some applications, for example microscopy, the signal is often too weak and needs to be amplified.

The indirect method is a two-step labeling method that results in signal amplification. It involves a primary antibody (first step) that binds to the target molecule in the sample and a labeled secondary antibody (second step) that binds to the primary antibody. Since several secondary antibody molecules bind to each primary antibody molecule, the signal is amplified. The secondary antibody is usually raised against the immunoglobulin class of the animal species in which the primary antibody has been raised. For example, if the primary antibody is a mouse IgG antibody, the secondary antibody is an anti-mouse IgG antibody that recognizes all mouse antibodies of the IgG class.

Although the indirect method is beneficial when it comes to signal amplification, it gives rise to unspecific signals due to unspecific binding of the secondary antibody to endogenous antibodies present in the sample. In addition, it is also often desired to further amplify the signal, especially in fluorescence microscopy where it is crucial to override the autofluorescence of the tissue sample. One last amplification step can be introduced by using a biotinylated secondary antibody and labeled streptavidin. Streptavidin binds tightly to biotin and since several biotin molecules are conjugated to each biotinylated antibody, amplification is achieved. However, biotin is also naturally present in biological samples, which causes unspecific binding of streptavidin to the sample, unless the endogenous biotin is blocked. Hence, an alternative signal amplifying system is desired that (1) does not cause background signal from endogenous antibodies/biotin, and that (2) enables more amplification steps.

So far only single immunolabeling has been described. Additional variants of unspecific antibody cross-binding arise when using the indirect method for multi-immunolabeling. By using primary antibodies made in different species, each primary antibody can be detected with a corresponding secondary antibody that recognizes the Ig class of the animal species of the primary antibody. For example if one primary antibody is made in rat and the other is made in rabbit, these two primary antibodies can be detected with one anti-rat and one anti-rabbit secondary antibody that are labeled with two different reporter molecules, for example two different fluorochromes. However, because most primary antibodies are made in a handful animal species (mostly mouse, rat, rabbit and goat), the probability of ending up with two primary antibodies of the same antibody class (species) greatly increases by each extra primary antibody that is included in the antibody panel for multi-immunolabeling of a sample. In addition, care must also be taken for each secondary antibody in the antibody panel, so that none of them belong to the same antibody class as any of the primary antibodies. Hence, because of this antibody cross-binding problem only a few primary antibodies can be amplified using the indirect method. Since the present invention does not cause antibody cross-binding it enables amplification of any number of primary antibodies.

SUMMARY OF THE INVENTION

According to an aspect of the invention, the above is at least partly alleviated by a method for preparing a biological sample for use in an immunolabeling process, the method comprising labeling the biological sample with a labeling component, the labeling component provided with a first enhancer antigen, and providing a first enhancer antibody, the first enhancer antibody selected to solely bind to the first enhancer antigen, wherein the first enhancer antigen is non-present in the immunolabeling process.

In accordance to the invention, a signal enhancer system for immunolabeling enables an unlimited number of amplification steps on top of a labeling component, for example being a primary antibody, without any antibody cross-binding. The absence of antibody cross-binding also enables any number of different labeling components (e.g. the labeling component and a plurality of additional labeling components, for example being different primary antibodies) to be combined for multi-immunolabeling, regardless of what animal species the primary antibodies are made from. The invention is based on carefully chosen antigens that are used as unique tags and corresponding antibodies that are used for detection of the tags. The antigens are chosen so that the antigen is non-present in immunolabeling process, i.e. not present in the biological sample and not present in reagents that are used in sample processing or staining reagents.

As such, when introducing the labeling component provided with the first enhancer antigen, the first enhancer antigen has not been previously introduced (or comprised) in the immunolabeling process. Neither is a similar (identical, corresponding) antigen to be introduced subsequently in the immunolabeling process. In addition, the antigen should not be present in any further components used in the immunolabeling process, for example including reporter molecule used in the immunolabeling process, such as fluorochromes, chromogens, enzymes, etc. The antigen should furthermore not be present in any antibody comprised with the sample or used with the immunolabeling process, and the antigen should not be present in biotin or streptavidin.

As mentioned above, the labeling component may preferably be a primary antibody conjugated with the first enhancer antigen. Alternatively, the labeling component may comprise a complex of a primary and a secondary antibody, the secondary antibody conjugated with the first enhancer antigen. Accordingly, this will allow the inventive concept to be used also in relation to already available direct and indirect methods of immunolabeling.

Still further, it may in accordance to the invention be possible to arrange the labeling component to comprise a complex of a biotinylated primary antibody and a streptavidin composition. It should be understood that the expression "streptavidin composition" should be interpreted broadly and to also include any streptavidin derivative, such as avidin, NeutrAvidin, traptavidin, or any monovalent deratives of these compounds. Advantages with using a monovalent streptavidin composition with only one functional binding site for biotin, avoids antibody aggregations e.g. during a mixing step in a liquid phase.

In a further possible embodiment according to the invention, the labeling component is a non-antibody protein or a carbohydrate with binding affinity for a certain structure in the sample. This may for example provide for the possibility of amplifying signals of different lectin molecules that are used to label certain cell types or phalloidin that are used to label actin cytoskeleton.

As understood from the above, the concept of the invention relies on the fact that the first enhancer antigen is not comprised with the sample or any reagents used in the immunolabeling process. The antigen may as such in accordance to some embodiments be seen as non-functional in relation to the sample, or in relation to immunolabeling process. Thus, it could be possible to consider using an antigen that is present on functional molecules in nature, however not in relation to the sample and/or the immunolabeling process. For example, some antigens present on molecules in bacteria or plants may be suitable. In some embodiments the antigen may be defines as being non-biological and non-present in mammalian species, however this is not a necessity in relation to the present invention.

In a preferred embodiment of the invention, the antigen may be formed from an artificially formulated peptide sequences that are not present in any proteins in nature, and thereby the artificial peptides may serve as unique antigens that are not present in any biological sample. Such non-biological peptides can be designed using protein sequence databases, such as the universal proteome database. The artificially formulated peptide sequence may then be used for forming the first enhancer antigen and for subsequent generation of a corresponding first enhancer antibody for use in relation to the present invention. In accordance to the invention, the enhancer antigens may be other molecules than peptides/proteins (such as for example carbohydrates, etc. as is well known for skilled addressee) and the enhancer antibodies used in the inventive process may be either monoclonal antibodies or polyclonal antibodies, depending in the cost and generation method.

As mentioned above, the inventive concept may be used for amplification, and thus the first enhancer antibody may in one embodiment be conjugated with a second enhancer antigen, wherein the second enhancer antigen is non-present in the immunolabeling process and different from the first enhancer antigen, the method further comprising the step of providing a second enhancer antibody, the second enhancer antibody selected to solely bind to the second enhancer antigen. The unlimited amplification will, as understood based on the above, allow for the second enhancer antibody to possibly be conjugated with a third enhancer antigen, the third enhancer antigen being non-present in the immunolabeling process and different from either of the first and the second enhancer antigen. The process may of course continue with a "chain" of further antigens/antibodies.

It is preferred to allow the "last" enhancer antibody in the chain to be labeled with a reporter molecule. Accordingly, the first as well as any further enhancer antibody may be provided with the reporter molecule. The reporter molecule is typically selected from a group comprising a fluorochrome, an enzyme, a peptide, quantum dots, and a transition metal. Other known or future reporter molecules are possible and within the scope of the invention, such as for example an oligonucleotide. The reporter molecule(s) are typically used in a subsequent detection/analysis process, such as for example by illumination of the biological sample under a microscope to detect a light from a fluorochrome. In such an embodiment the reporter element is preferably a fluorochrome.

The inventive concept has been described in relation to the use of a single labeling component used for labeling the biological sample. However, since the first enhancer antigen as selected in accordance to the inventive concept does not bind any labeling components, including antibodies, streptavidin or proteins used for labeling, the inventive concept may also be used in a multi-immunolabeling process, where more than one labeling component is used for labeling the biological sample. Accordingly, in an embodiment of the invention the method further comprises labeling the biological sample with an additional labeling component, the additional labeling component provided with an additional first enhancer antigen, and providing an additional first enhancer antibody, the additional first enhancer antibody selected to solely bind to the additional first enhancer antigen, wherein the additional first enhancer antigen is non-present in the immunolabeling process. Thus, the inventive concept will essentially allow for the immunolabeling of a biological sample with an unlimited number of labeling components.

As the first enhancer antigens/first enhancer antibodies used in the multi-immunolabeling process are selected to be different from each other (as well as not previously or subsequently present in the immunolabeling process), the inventive concept allows for the use of a single first enhancer antibody for each of the different labeling components. The inventive concept also allows for the use of a chain of enhancer antibodies as discussed above. In any case, it is preferred, as above, that the last antibody in the chain is provided with a reporter molecule. In the present embodiment provided in relation to a multi color immunolabeling process, it is of course preferred that the reporter molecules are selected to generate different signals that can be separated in a subsequent analysis process.

According to another aspect of the invention there is provided a kit for use in an immunolabeling process, the kit comprising a first enhancer antibody, and a first enhancer antigen conjugated to a labeling component to be used for labeling a biological sample, wherein the first enhancer antibody is selected to solely bind to the first enhancer antigen, the first enhancer antigen being non-present in the immunolabeling process.

As understood, the kit may be arranged such that labeling component is a primary antibody conjugated with the first enhancer antigen, such that the labeling component comprises a complex of a primary and a secondary antibody, the second antibody conjugated with the first enhancer antigen, or such that the labeling component comprises a complex of a biotinylated primary antibody and a streptavidin composition. Similarly, a chain of antibodies may be formed.

In accordance with the invention, it may also be possible to arrange the kit to comprise a plurality of different first enhancer antibodies selected as discussed above, specifically allowing for use in a multi-immunolabeling process. The kit according to the invention may also comprise the above discussed labeling component provided with the first enhancer antigen, e.g. the primary antibody conjugated with the first enhancer antigen, etc. According to still another aspect of the invention there is provided a kit for use in an immunolabeling process, the kit comprising a first enhancer antibody, wherein the first enhancer antibody is selected to solely bind to a first enhancer antigen of a labeling component to be used for labeling a biological sample, the first enhancer antigen being non-present in the immunolabeling process, and an additional first enhancer antibody, wherein the additional first enhancer antibody is selected to solely bind to an additional first enhancer antigen of an additional labeling component to be used for labeling of the biological sample, the additional first enhancer antigen being non-present in the immunolabeling process, the first enhancer antigen being different from the additional first enhancer antigen. This is further elaborated below in the detailed description of the invention.

Still further, in another aspect of the invention there is provides a kit for use in an immunolabeling process, the kit comprising a first enhancer antibody conjugated with a second enhancer antigen, wherein the first enhancer antibody is selected to solely bind to a first enhancer antigen of a labeling component to be used for labeling a biological sample, the first and the second enhancer antigens being non-present in the immunolabeling process. This is further elaborated below in the detailed description of the invention.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1:
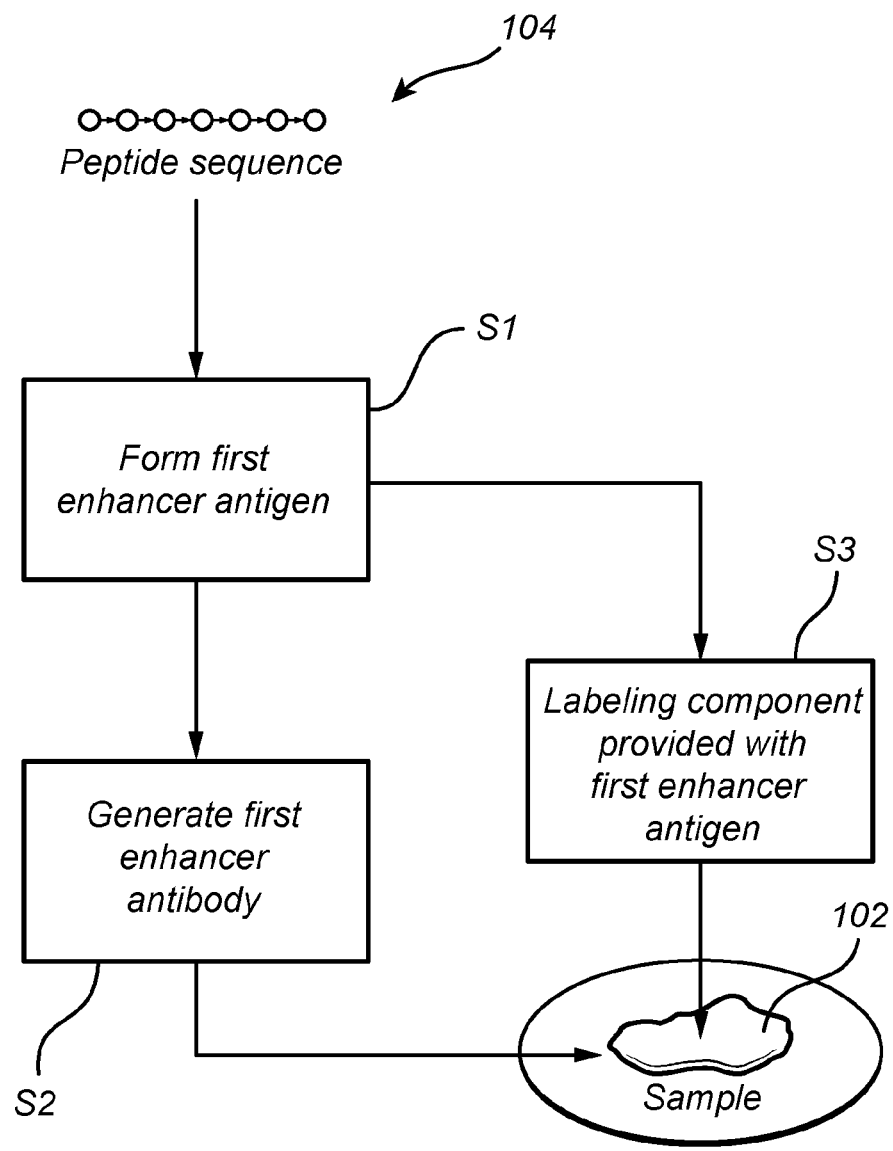
FIG. 1 conceptually illustrates the method steps according to the invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Referring now to the drawings and to FIG. 1 in particular, there is exemplified a process of preparing a biological sample 102 for use in an immunolabeling process. As a first step, a first enhancer antigen is selected in accordance to the criteria defined in accordance to the invention. That is, the first enhancer antigen should be previously (or subsequently) non-present in the immunolabeling process. Accordingly, the first enhancer antigen should not be present in the biological sample and not present in reagents that are used in sample processing or staining reagents. In addition, the antigen should not be present in any further components used in the immunolabeling process, for example including reporter molecule used in the immunolabeling process, such as fluorochromes, chromogens, enzymes, etc. The antigen should furthermore not be present in any antibody comprised with the sample or used with the immunolabeling process, and the antigen should not be present in biotin or streptavidin.

The selection process for the first enhancer antigen may be such that it is formed, S1, from a preselected peptide sequence 104, for example artificially formulated in a computerized process. The process for selecting the peptide sequence 104 as well as the formation of the first enhancer antigen from such a preselected peptide sequence involves numerous steps being well known to the skilled addressee and are therefore not further discussed. The antigen may also be non-peptide molecules.

Once the first enhancer antigen successfully has been formed, two separate steps are taken, including generating, S2, of a first enhancer antibody based on the first enhancer antigen, and providing, S3, a labeling component that is tagged with the first enhancer antigen. The generation process for the first enhancer antigen and first enhancer antibody also includes a plurality of steps known to the skilled addressee, including for example choice of immunogenic antigen, adjuvants, host animal, immunization, antibody selection, antibody purification, etc.

As discussed above, the labeling component may for example be a primary antibody, where the first enhancer antigen has been conjugated with the primary antibody. The primary antibody binds directly to a target antigen comprised with the biological sample 102, once being introduced with the biological sample 102. Hence, the primary antibody is selected dependent on what type of target antigen comprised with the biological sample 102 that subsequently is to be detected/analyzed in e.g. an immunofluorescence process. As discussed, the primary antibody has been conjugated with the first enhancer antigen, and the first enhancer antibody has been generated based on the same first enhancer antigen. Thus, once the first enhancer antibody is introduced to the biological sample 102, the first enhancer antibody will solely bind to the first enhancer antigen provided with the first enhancer antigen.

Figure 2:
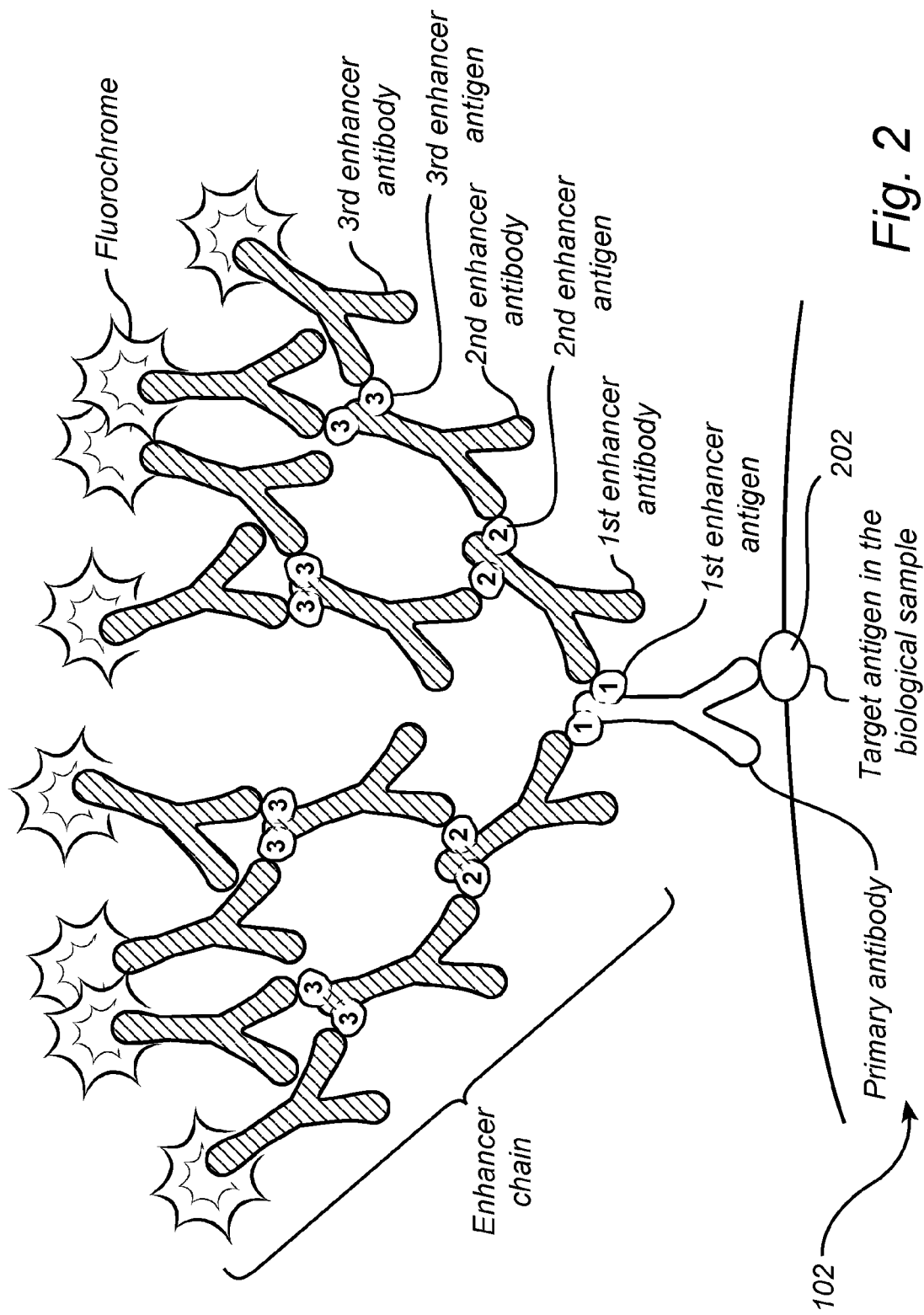
FIG. 2 shows signal amplification during immunolabeling of a sample using an enhancer chain in accordance to a preferred embodiment of the invention.
Figure 3:
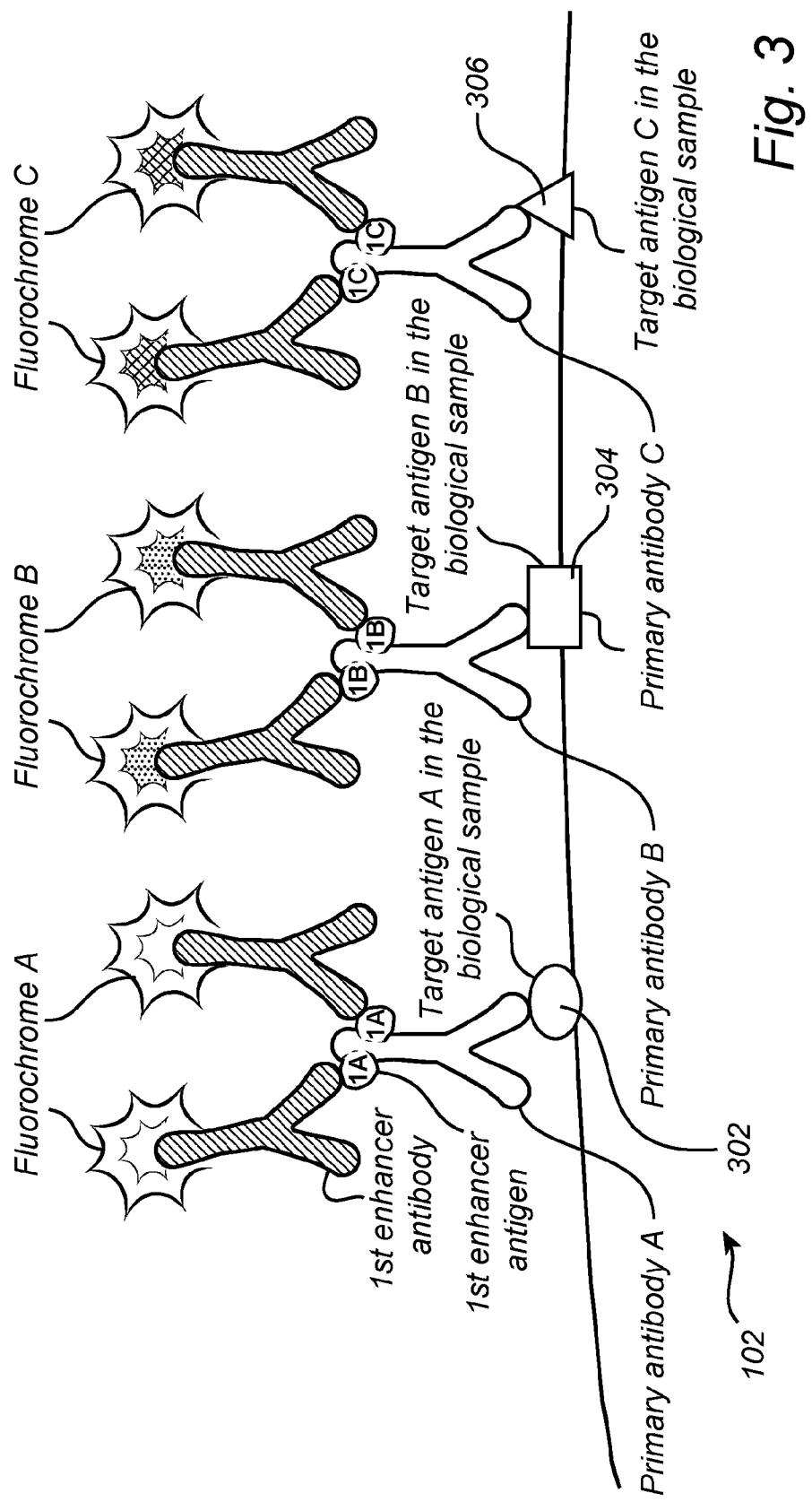
FIG. 3 shows multi-immunolabeling of a sample in accordance to the invention.

The first enhancer antibody may be utilized in different ways dependent on the application at hand, as will be exemplified in FIGS. 2 and 3. For example, and as is illustrated in FIG. 2, it may in accordance to the invention be possible to form an enhancer chain for "amplifying" the detection of a target antigen 202 in the biological sample 102.

As is shown in FIG. 2, the enhancer chain may comprise a plurality of enhancer steps, i.e. where the first enhancer antibody has been provided (conjugated) with a second enhancer antigen selected and formed in a similar process as discussed above, as well as again taking into account the criteria set for the selection of antigen. The enhancer chain could thus be arranged to include an in essence unlimited number of enhancer steps, e.g. second, third, fourth, etc., enhancer antibody/antigen forming an expanding "three structure".

As discussed above, it is desirable to provide the last enhancer antibody in the chain (in FIG. 2 being the third enhancer antibody) with a reporter molecule, such as for example a fluorochrome. Other reporter molecules are possible, including for example an enzyme, a peptide, quantum dots, or a transition metal. Providing an antibody with a reporter molecule such as a fluorochrome is process known to the skilled addressee.

Turning now to FIG. 3, where the biological sample 102 has been prepared in accordance to a multi-immunolabeling process, where a first 302, a second 304 and a third 306 target antigen is to be subsequently detected/analyzed.

In a similar manner as discussed above, a primary antibody is selected for each of the target antigens 302, 304, 306, in FIG. 3 denoted as primary antibodies A, B and C. A first enhancer antigen 1A is formed and provided with the primary antibody A, a first enhancer antigen 1B is formed and provided for the primary antibody B, etc. Similarly, corresponding first enhancer antibodies are generated for each of the first enhancer antigens 1A, 1B, 1C.

Each of the first enhancer antibodies are provided with a different reporter molecule, such as with different fluorochromes generating lighting within different wavelength ranges, thus making detection and analysis of each of the target antigens 302, 304, 306 possible. It would of course be possible, and within the scope of the invention, to form enhancer chains for each of the target antibodies 302, 304, 306, in a similar manner as shown in FIG. 2. Also, the concept discussed above e.g. in relation to FIGS. 2 and 3 could of course be combined with known multi-immunolabeling processes, e.g. where the reporter molecules are on one or a plurality of primary antibodies, secondary antibodies or streptavidin (i.e. "prior-art" direct and indirect immunolabeling methods), and the concept involving the inventive enhancer antigens/antibodies are used for detection of one or a plurality of additional target antigens of the biological sample (still taking into consideration the antigen selection criteria as defined in accordance to the invention).

Based on the above explanation and elaboration, it should be apparent for the skilled addressee that it is advantageous to prepare an immunolabeling kit for use in preparing of a biological sample. The kit should in accordance to the invention comprise a first enhancer antibody, where the first enhancer antibody is selected to solely bind to a first enhancer antigen of a labeling component to be used for labeling a biological sample, the first enhancer antigen being non-present in the immunolabeling process. The kit may of course comprise a plurality if first enhancer antibodies formed in accordance to the above discussion and each being based on a specifically selected first enhancer antigen. Each of the enhancer antibodies may be provided with a reporter molecule, or each provided with a second enhancer antigen for allowing the formation of a plurality of enhancer chains as discussed above.

In summary, the present invention relates to a method for preparing a biological sample for use in an immunolabeling process, the method comprising labeling the biological sample with a labeling component, the labeling component provided with a first enhancer antigen, and providing a first enhancer antibody, the first enhancer antibody selected to solely bind to the first enhancer antigen, wherein the first enhancer antigen is non-present in the immunolabeling process.

The invention is based on the understanding that a signal enhancer system may be provided for immunolabeling that allows an unlimited number of amplification steps on top of a labeling component, for example being a primary antibody, without any antibody cross-binding. The absence of antibody cross-binding also enables any number of different labeling components (e.g. the labeling component and a plurality of additional labeling components, for example being different primary antibodies) to be combined for multi-immunolabeling, regardless of what animal species the primary antibodies are made from.

The invention is based on carefully chosen antigens that are used as unique tags and corresponding antibodies that are used for detection of the tags. The antigens are chosen so that the antigen is non-present in immunolabeling process, i.e. not present in the biological sample and not present in reagents that are used in sample processing or staining reagents.

Although the figures may show a specific order of method steps, the order of the steps may differ from what is depicted. Also two or more steps may be performed concurrently or with partial concurrence. Such variation will depend on designer choice. All such variations are within the scope of the disclosure. Additionally, even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:
1. A method for preparing a biological sample for use in an immunolabeling process, the method comprising:
    labeling the biological sample with a labeling component, the labeling component provided with a first enhancer antigen, providing a first enhancer antibody, the first enhancer antibody selected to solely bind to the first enhancer antigen, and providing a second enhancer antibody, the second enhancer antibody selected to solely bind to a second enhancer antigen, wherein the first enhancer antigen is formed from an artificially formulated peptide sequence that is not present in any proteins in nature and is non-present in the biological sample or any reagents used in the immunolabeling process other than the labeling component, wherein the first enhancer antibody is conjugated with the second enhancer antigen, and wherein the second enhancer antigen is formed from artificially formulated peptide sequences that are not present in any proteins in nature, is non-present in the biological sample or any reagents used in the immunolabeling process other than the labeling component, and is different from the first enhancer antigen.

2. The method according to claim 1, wherein the labeling component is a primary antibody conjugated with the first enhancer antigen.

3. The method according to claim 1, wherein the labeling component comprises a complex of a primary and a secondary antibody, the secondary antibody conjugated with the first enhancer antigen.

4. The method according to claim 1,
wherein the labeling component comprises a complex of a biotinylated primary antibody provided with a streptavidin composition, or wherein the labeling component comprises a complex of a primary antibody and a biotinylated secondary antibody provided with a streptavidin composition, wherein the streptavidin composition is conjugated with the first enhancer antigen.

5. The method according to claim 4, wherein the streptavidin composition is a monovalent streptavidin composition.

6. The method according to claim 1, wherein the first enhancer antibody is labeled with a reporter molecule.

7. The method according to claim 1, wherein the second enhancer antibody is labeled with a reporter molecule or conjugated with a third enhancer antigen, the third enhancer antigen being non-present in the immunolabeling process and different from either of the first and the second enhancer antigen.

8. The method according to claim 6, wherein the reporter molecule is selected from a group consisting of a fluorochrome, an enzyme, a peptide, quantum dots, and a transition metal.

9. The method according to claim 6, wherein the reporter molecule is an oligonucleotide.

* * * * *